United States Patent [19]
Slee

[11] Patent Number: 5,062,709
[45] Date of Patent: Nov. 5, 1991

[54] PROCESS FOR MONITORING PARTICLE SIZE AND MOISTURE CONTENT OF FINELY DIVIDED MATERIAL

[75] Inventor: James D. Slee, Naperville, Ill.

[73] Assignee: Amoco Corporation, Chicago, Ill.

[21] Appl. No.: 514,504

[22] Filed: Apr. 25, 1990

[51] Int. Cl.[5] ............................................. G01N 15/02
[52] U.S. Cl. ..................................... 356/335; 356/446
[58] Field of Search ........................ 356/335, 446, 336

[56] References Cited

U.S. PATENT DOCUMENTS

| | | | |
|---|---|---|---|
| 4,040,747 | 8/1977 | Webster | 356/446 |
| 4,752,689 | 6/1988 | Satake | 356/446 |
| 4,755,048 | 7/1988 | Kaufman | 356/407 |

OTHER PUBLICATIONS

Klochko et al., "Photometric Method of Estimating the Particle Size of Carbon Black", *Industrial Laboratory*, vol. 39, No. 5, pp. 753–755.

Primary Examiner—Richard A. Rosenberger
Attorney, Agent, or Firm—Gunar J. Blumberg; William H. Magidson; Ralph C. Medhurst

[57] ABSTRACT

The instant invention relates to a process for monitoring the particle size and moisture content of finely divided material employing the reflectance of scattered light. The invention is particularly directed to monitoring the particle size within limits and moisture content of terephthalic acid after crystallization and drying processes. The invention is futther directed to providing feedback signals to control dryer throughput and dryer temperature to control moisture content of the finely-divided material.

14 Claims, 4 Drawing Sheets

PROCESS FOR MONITORING PARTICLE SIZE AND MOISTURE CONTENT OF FINELY DIVIDED MATERIAL

This process relates to a process for monitoring particle size and/or moisture content of any finely divided material which reflects light sufficient for detection by a photodector wherein the light is of a wavelength within the range of from about 350 nanometers (nm) to about 1200 nm. This process relates to a process for monitoring any finely divided material wherein particle size is less than about 300 microns and moisture present is no more than about 10 wt. percent of the finely divided material.

This invention also relates to a continuous monitoring process for downstream measurement of particle size and moisture contained in these particles in production of terephthalic acid wherein the terephthalic acid has been purified by crystallization and dried to reduce moisture content. The moisture is present as surface moisture on the particles. The invention further relates to a continuous monitoring process for standardization of product containing a specified level of particle size wherein the level of particle size is monitored within required limits. The invention also relates to a continuous method to control dryer temperature and throughput rate to maintain a specified level of moisture content in dryer product.

BACKGROUND OF THE INVENTION

Large amounts of finely divided material are routinely produced in industrial processes wherein particle size and/or moisture content within narrow limits are of importance. For example, chemical compounds typically react more readily in a finely divided state. The presence of water can be a factor in a chemical reaction. Accordingly, the characterization of a finely divided material can include limits as to particle size and water content within narrow limits. However, the determination of particle size and water content wherein the particles are of micron size by other than laboratory procedures is not easily obtained under production conditions. Typical of these materials produced in large quantities wherein particle size and moisture content are important are di- and tricarboxylic acids, polymers such as polyethylene and polypropylene. as well as others too numerous to mention.

Large amounts of aromatic di- and tricarboxylic acids are produced commercially by the oxidation of the alkyl aromatic compounds. Several different oxidation processes are known, with examples set forth in Volume 17, pages 732-777 of Kirk-Othmer's *Encyclopedia of Chemical Technology*, John Wiley and Sons, (1982). High molecular weight polyesters of these aromatic di- and tricarboxylic acids with various diols find extensive use in many applications. For example, high molecular weight polyesters of terephthalic acid have long been prepared of the Dacron TM, Terylene TM, and Kodel TM type fibers, and Mylar TM film, as described in U.S. Pat. No. 2,465,319 by transesterification of dimethylterephthalate with the appropriate gylcol followed by polycondensation. With the advent of improved processes for the manufacture of terephthalic acid of exceptionally high purity, the preparation of polyesters of terephthalic acid by direct esterification of terephthalic acid with glycol to a large extent has replaced dimethylterephthalate as a highly desirable alternate procedure.

This has manifest advantages of simplicity and economy as compared with the dimethylterephthalate route. Large quantities of terephthalic acid of suitable purity, free from contaminants are produced in a high-volume production procedure. Typically, many thousands of pounds of product are produced within a short period of hours. Analyses for contaminants by typical laboratory procedures can handicap high volume production.

Terephthalic acid is produced by the catalytic oxidation of paraxylene with molecular oxygen. Terephthalic acid is purified by a second process which consists of 1) catalytic hydrogenation to reduce certain oxidation by-products and 2) recrystallization to remove impurities. Water is used as a solvent. Because terephthalic acid is only sparingly soluble in water at ambient temperatures and pressure, but is soluble at high temperature and pressure, temperatures in the range of from about 400° F. to about 700° F. are used with high pressure. The difficulties of obtaining representative samples during the course of the process are obvious.

Crystal size is determined by crystallization temperature and concentration of terephthalic acid in the aqueous solution. Two or more crystallization stages are frequently used. Procedures for crystallization and extraction are taught in U.S. Pat. Nos. 3,082,250; 3,452,088; 3,497,552; 3,505,398; and 3,931,305, among others.

Esterification of terephthalic acid with a glycol is affected by particle size of the terephthalic acid. Particle size of the terephthalic acid also affects material handling characteristics of the material since the amount of so-called fines affects the bulk density of the material and the related properties such as the packing characteristics.

With the advent of optical analysis of impurity absorptions to determine impurity components present in both homogeneous and nonhomogeneous light scattering materials, see U.S. Pat. No. 4,755,048, much attention has been directed to determining levels of contaminants and particle size of materials present.

For example, the use of a laser beam in an apparatus for measuring particle size of particles in a fluid stream is taught in EP Patent No. 350768. Particle size and velocity measurement by measuring light scatter from a laser beam is taught in U.S. Pat. No. 4,854,705. Particle size in a liquid stream using a beam of light and recording radiation scattering is disclosed in SU Patent 1,448,246. The size of solid particles in a liquid phase is measured to control the size of the particles to allow continuous control of particle size in manufacture of a non-aqueous liquid cleaning product by the method of GB Patent 2,219,002.

Although the methods and instrumentation presently known in the art find widely differing applications, there is a need for a method to monitor in a production line the particle size of a material in a dry state wherein the particle size is from about 1 to 300 microns, and moisture content is a maximum of about 10 wt. %. In the case of terephthalic acid, variations in particle size within the range of from about 10 to 50 microns can be determined by very sophisticated reflectance spectrophotometric equipment such as Microtrac TM, supplied by Leeds & Northup, St. Petersburg, Fla. However, this requires a laboratory procedure, poorly suited for an on-line analysis for a continuous production line for a critical product. Typically, thousands of pounds of product are prepared during the interval between analyses.

It is an object of this invention to provide a method for monitoring particle size of finely divided material, the particles of which range in size from about 1 micron to about 300 microns.

It is an object of this invention to provide a process for monitoring moisture content of finely divided material of up to about 300 microns in size and contains up to about 10 wt. percent moisture.

It is an object of this invention to provide a method for monitoring particle size of finely divided material in a series of samples, the particles of which, in part, range in size from about 1 micron to about 300 microns.

It is an object of this invention to provide an on-line method for continuous or periodic monitoring of particle size and/or moisture content of finely divided particles of up to about 300 microns in size and containing up to about 10 wt. % moisture.

It is an object of this invention to provide a continuous method for monitoring particle size of on-line production of terephthalic acid wherein said terephthalic acid comprises finely-divided material, the particles of which, in part, range in size from about 10 to about 50 microns.

It is an object of this invention to provide a continuous method for monitoring moisture content of particles of on-line production of terephthalic acid wherein said terephthalic acid comprises finely-divided material, the particles of which, in part, range in size from about 10 to about 50 microns.

SUMMARY OF THE INVENTION

This invention relates to a process for monitoring particle size and moisture content of finely-divided material, the particles of which, in part, range in size from about 1 micron to about 300 microns and moisture content is up to about 10 wt. %. The process is suitable for monitoring on-line production of material by continuous monitoring a series of samples as to particle size and moisture content employing the reflectance of scattered light. The process is especially suitable for measuring particle size and control of moisture content of terephthalic acid in an on-line continuous production procedure wherein the terephthalic acid is the product of steps involving crystallization and drying. Dryer temperature and through-put rate can be continuously controlled to maintain a specified moisture content of terephthalic acid.

DETAILS OF THE INVENTION

This invention relates to a process for monitoring particle size and moisture content of finely divided dry material by measuring the intensity of scattered visible light of a wavelength of from about 350 nanometers (nm) to about 1200 nm. This invention relates to a continuous process for monitoring particle size and/or moisture content of finely divided material which reflects light sufficient for detection by a photodetector. Particle size is 300 microns or less, and moisture content is no more than 10 wt. %. This invention is particularly related to the continuous monitoring of particle size and moisture content of terephthalic acid (TA) wherein the particle size of the TA, in part, ranges from about 10 microns to about 50 microns, in an amount which is from about 2 wt. % to about 50 wt. % of the TA, and moisture content is in the range of from about 0.01 wt. % to about 7 wt. %. This invention is directed further to an improved method to control moisture content of TA obtained as product from a process of crystallization to improve purity followed by a process of drying to remove moisture. This invention further relates to an improved method of using an optical sensor apparatus employing the reflectance of scattered visible light of a wavelength of from about 400 nm to about 750 nm to measure particle size and particle moisture content of TA. The monitoring of particle size and moisture content can be performed continuously or periodically by the process of the instant invention.

Surprisingly, it has been found that light scattering of the light transmission of a wavelength between 350 nm and 1200 nm correlates with particle size wherein particle size is in the range of from 1 to 300 microns.

Surprisingly, it has been found that the intensity of scattered light, as measured by the voltage generated by a photodetector, of a wavelength of from about 450 nm to about 750 nm, preferably from about 550 nm to about 750 nm, more preferably 710 nm, correlates inversely with particle size of dry TA wherein the particle size is in the range of from about 10 microns to about 50 microns.

Surprisingly, it has also been found that the standard deviation of measurements of voltage generated by the intensity of scattered light, as measured by the voltage generated by a photodetector, of a wavelength within the range of from about 400 nm to about 750 nm correlates with moisture content of TA. Hereinafter, this relationship of the standard deviation of voltage generated by a photodetector, in measuring light intensity reflected from TA, to moisture content of the TA will be referred to as the standard deviation wavelength voltage (SDWV) of terephthalic acid.

The intensity of scattered light of any wavelength within the range of from about 400 nm to about 750 nm can be used to determine the SDWV of terephthalic acid. However, in normal operation, the yellowness of TA is routinely determined by measuring the b-value at wavelengths of 450 nm, 550 nm and 710 nm. Conveniently, the wavelengths of 450 nm, 550 nm and 710 nm can also be used to determine moisture content.

As is well known, the b-value has been described by Richard S. Hunter in *The Measurement of Appearance*, John Wiley & Sons (New York), 1975, pages 122–123.

In the case of TA, variations in the b-value are typically less than the human eye can see, thus requiring very sophisticated reflectance spectrophotometric equipment for its measurement by intensity of reflected light. Means are generally available for measuring light reflectance intensity. However, in the prior art there has been no recognition of the possibility and/or utility of using scattered light intensity of a wavelength of from about 400 nm to about 750 nm to measure particle size of TA or of using the standard deviation of measurements of voltages generated by a photodetector of intensity of scattered light at wavelengths within the range of from about 400 nm to about 750 nm as a measure of moisture content of TA particles in a process stream to control moisture content of a dryer output.

It is noted that although the following is directed to measurement of particle size and moisture content of TA, the invented process can be used to monitor continuously particle size and moisture content of any material which reflects scattered light sufficient for detection by a photodetector where particle sizes are no greater than about 300 microns and moisture content is no greater than about 10 wt. %.

Examples of such materials include trimellitic acid, phthalic acid, 2,6-naphthalene dicarboxylic acid, trimellitic anhydride, phthalic anhydride, benzoic acid and other organic acids. Such materials also include polymers such as polypropylene and polyethylene as well as clays and inorganic materials such as talc, etc.

Moisture content relates to any liquid capable of wetting, covering or soaking a finely-divided material by penetration of pores or interstices of the finely-divided material. Although the following is directed to measurement of moisture principally comprising water, the moisture present can comprise any organic acid of from 2 to 8 carbon atoms, especially acetic acid, alcohols of from 1 to 12 carbon atoms, polyols of from 2 to 16 carbon atoms and hydroxyterminated esters and ethers having molecular weights of up to about 500.

A sensor apparatus useful in the process of this invention is disclosed and taught in U.S. Pat. No. 4,755,048, although other sensor apparatus which perform similar functions can be adapted to the process of the instant invention. Since the process of the instant invention continuously monitors particle size and moisture content of finely divided dry material, it is essential that the sampling means incorporated with the sensor apparatus be able to continuously, or periodically within short time periods, obtain product samples representative of the product stream. It is further desirable that the SDWV of TA as measured by an optical sensor furnish a means of producing a feedback signal from the signal processing system to control dryer throughput and drying temperatures of TA.

The sampling means of this invention in monitoring production of TA can comprise a V-shaped receptacle mounted in the process stream from the TA dryer. The receptacle can be equipped with a means of dislodging quantities of TA gathered from the product stream by the movement of the TA streams. The means of dislodgement can be an air jet which is periodically or continuously activated to disperse the TA contained in the receptacle. It is not necessary that the receptacle be a bottom-closed unit but only that the receptacle be so designed, e.g., incorporating a screen of adequate mesh, to provide a means for product buildup and thus provide a sample of material passing the receptacle.

The sensor apparatus of this invention requires (a) a source of light which affords useful wavelengths; (b) a vessel or other suitable means to hold the product sample; (c) a spectrophotometric analyzer comprising an array of photodetectors, fitted with appropriate filter elements; and (d) a signal processor system for quantifying the observed intensities of selected wavelengths characteristic of the scattered light. The sensor apparatus further requires communications means for transmitting light to the product sample, collecting selected wavelengths of reflected scattered light, and transmitting the selected wavelengths to the signal processor system. The invention of this disclosure preferably utilizes optical fiber elements, either singly or in a plurality contained within a cable, as the means for communication of light to the sequence of critical members comprising the sensor apparatus. Selected optical fibers, generally comprising glass or fused quartz, possess the ability to repeatedly reflect light internally at their walls with negligible loss along the length of the fibers.

The light source employed in this invention will depend upon the selection of the wavelength or wavelengths of scattered light taken as characteristic of the product sample and the impurities to be quantified. Generally, the reference light source is a polychromatic light having useful wavelengths within the range from about 350 nm to about 1,200 nm, preferably from about 350 nm to about 1,000 nm, thus embracing the visible and near-infrared spectral regions.

The spectrophotometric analyzer of this invention may be any such instrument having a plurality of photodetectors, preferably silicon photodiodes, each receiving a selected wavelength of the scattered light and transmitting the characterization thereof to the signal processor means. In turn, the signal processor responds to the characterization of the respective wavelengths, as, for example, by intensity of the signal, to quantify the concentration level of the sample components as determined by optical absorption.

There must be a sufficient number of elements transmitting scattered light to the analyzer to provide characterizations of the sample components and the product, the latter providing a characterization of the scattered light to correct for differences in concentration and distribution of the product as a function of time. There must also be provided an element measuring light intensity at a wavelength where there is absorption from either sample components or product. Accordingly, one or more wavelengths can be used to measure a nonhomogeneous dispersed system, depending upon components present. Thus, a simple unit for the practice of this invention need employ only one wavelength with an appropriate optical interference filter and individual silicon diodes or detectors to measure particle size and moisture content of PTA.

The sensor apparatus which can be utilized in this invention does not directly measure the particle size or moisture content of the TA samples but rather the intensity of scattered light at a selected wavelength of from 350 nm to about 1200 nm, preferably either at 450 nm, or 550 nm or 710 nm. These measurements are correlated with the particle size and/or moisture content using routine statistical methods wherein light intensities at the given wavelengths are given by voltage outputs.

As illustrated in FIG. 1, the voltage intensity of reflected light at 710 nm was found to be inversely related to the percent particles of a size of from about 10 microns to about 50 microns in purified terephthalic acid (PTA). As the percentage of fine particles which passed through a No. 325 mesh screen increased, the intensity of reflected light decreased. ASTM 11-87 covers the design and construction of No. 325 (45 micron) sieve.

As illustrated in FIG. 2, the standard deviation of measurements of the on-line output voltage of 450 nm correlate with PTA moisture from 0 wt. % to about 5 wt. % moisture.

FIGS. 3 and 4 illustrate that the standard deviation of the on-line voltages of 550 nm and 710 nm correlate with PTA moisture from 0 wt. % to about 5 wt. %.

In the application of this invention, the measurements of on-line SDWV, as calculated by an in-line reading of output voltages at wavelengths of from about 400 to about 750 nm, are related to moisture content of the PTA dryer output. Adjustment of dryer through-put rate and dryer temperature can be made manually or electronically to control moisture of PTA dryer output. The SDWV accordingly comprises a feedback signal to control dryer through-put rate and PTA dryer temperature.

In summary, the instant invention comprises a process for on-line monitoring of particle size and moisture content, of finely-divided material in a product stream wherein the said material reflects scattered light sufficient for detection by a photodetector, wherein the light is of a wavelength within the range of from about 350 nanometers to about 1200 nanometers, particle size of said material is from about 1 micron to about 300 microns, and moisture content is no greater than 10 weight percent of said material, which process comprises:

a) a sampling means comprising a sampling vessel located in said product stream wherein said sampling vessel contains a discharge means to discharge contents of said sampling vessel continuously or periodically;

b) a reference light source;

c) a spectrophotometric analyzer having a plurality of photodetectors for the characterization of wavelengths of scattered light within the range of from about 350 nm to 1200 nanometers;

d) a communication means having a first end connected to the light source and a second end extending into the sampling means;

e) a light transmission means capable of transmitting scattered light of wavelengths from about 350 nanometers to about 1200 nanometers from the sampling means to the plurality of photodetectors within the spectrophotometeric analyzer;

f) a signal processor means in communication with the plurality of photodetectors for processing the characteristics of the said wavelengths to quantify the photoelectric responses in volts to i) measure the percent particles of a particle size of said finely-divided material within the range of from about 1 micron to about 300 microns, as measured by the voltage generated by a photodetector which measures the intensity of scattered light of a wavelength within the range of from about 350 nanometers to about 1200 nanometers; and (ii) to measure the moisture content of said finely-divided material by the standard deviation of measurements of voltages generated by a photodetector which measures the said intensity of said scattered light of at least one wavelength within the range of from about 350 nanometers to about 1200 nanometers.

In more detail, said finely-divided material is selected from the group consisting of terephthalic acid, trimellitic acid, phthalic acid, 2,6-naphthalene dicarboxylic acid, trimellitic anhydride, phthalic anhydride, benzoic acid, polypropylene, polyethylene and clays wherein said finely-divided material comprises particles of 300 microns or less in size. The said finely-divided material can contain moisture of up to about 10 wt. %. The said moisture is selected from the group consisting of water, liquid organic acids of from 2 to 8 carbon atoms, alcohols of from 1 to 12 carbon atoms, polyols of from 2 to 16 carbon atoms, hyboxy-terminated esters and ethers having molecular weights of up to about 500, and mixtures thereof. Preferably, the said moisture is selected from the group consisting of water, acetic acid and mixtures thereof.

The instant invention preferably relates to a process of wherein said finely-divided material is terephthalic acid. The percent particles of particle size of from about 10 microns to about 50 microns of said terephthalic acid is measured by voltage generated by said photodetector in measuring intensity of scattered light of at least one wavelength within the range of from about 400 nanometers to about 750 nanometers, preferably from about 550 nanometers to about 710 nanometers, more preferably at 710 nanometers.

In more detail, the process of the instant invention measures percent particles of particle size passing a No. 325 mesh screen in the range of from about 2 wt. % to about 50 wt. % of total weight of said terephthalic acid. Moisture content of said terephthalic acid, is within the range of from about 0.01 wt. % to about 7.0 wt. % of total weight. Moisture content is measured by the standard deviation of measurements of voltages generated by a photodetector, which measures intensity of scattered light of at least one wavelength within the range of from about 400 nanometers to about 750 nanometers. Typically, the moisture content of said terephthalic acid comprises water. The said terephthalic acid typically is a product of a drying process and said standard deviation of said measurements generated by said photodetector comprises a feedback signal to control throughput rate and drying temperature of the drying process. The said feedback signal can be applied to the drying process continuously to control said throughput rate and said drying temperature. The sampling means can comprise a receptacle mounted in the process stream to provide continuous or intermittent means of sampling the process stream.

The feedback signal can be applied to the drying process by means well-known in the art, either continuously or periodically.

The following examples are illustrative without limitation of the invention of this disclosure:

EXAMPLE I

Sensor apparatus was assembled including a tungsten halogen lamp, a ⅛" fiber optic cable leading from the lamp to a flat optical head and a ¼" fiber optic cable leading away from the flat optical head. The optical head comprised a flat aluminum plate having holes drilled to receive the respective fiber optic cables in a parallel arrangement, said holes being spaced on ⅜" centers. The ¼" cable was also attached to an optical spectrophotometric multichannel analyzer (Princeton Instruments) which, in turn, was connected to an IBM AT computer and associated printer. The flat optical sensor head interfaced with a PTA powder sample employed in determining the b-value. The band width of the optical filters was 40 nm.

The scattered light emission spectrum was measured over the range from 400 nm to 730 nm. The b-value was measured using wavelengths at 450 nm, 550 nm and 710 nm. The ratio of wavelengths of 450 nm to 550 nm gave the best correlation to b-value. A wavelength of 710 nm was found to be the maximum of one of three carbon-hydrogen stretch overtone bands of PTA. A significant intensity of scattered light, with no significant optical absorption, was found at 550 nm.

Figure 1:
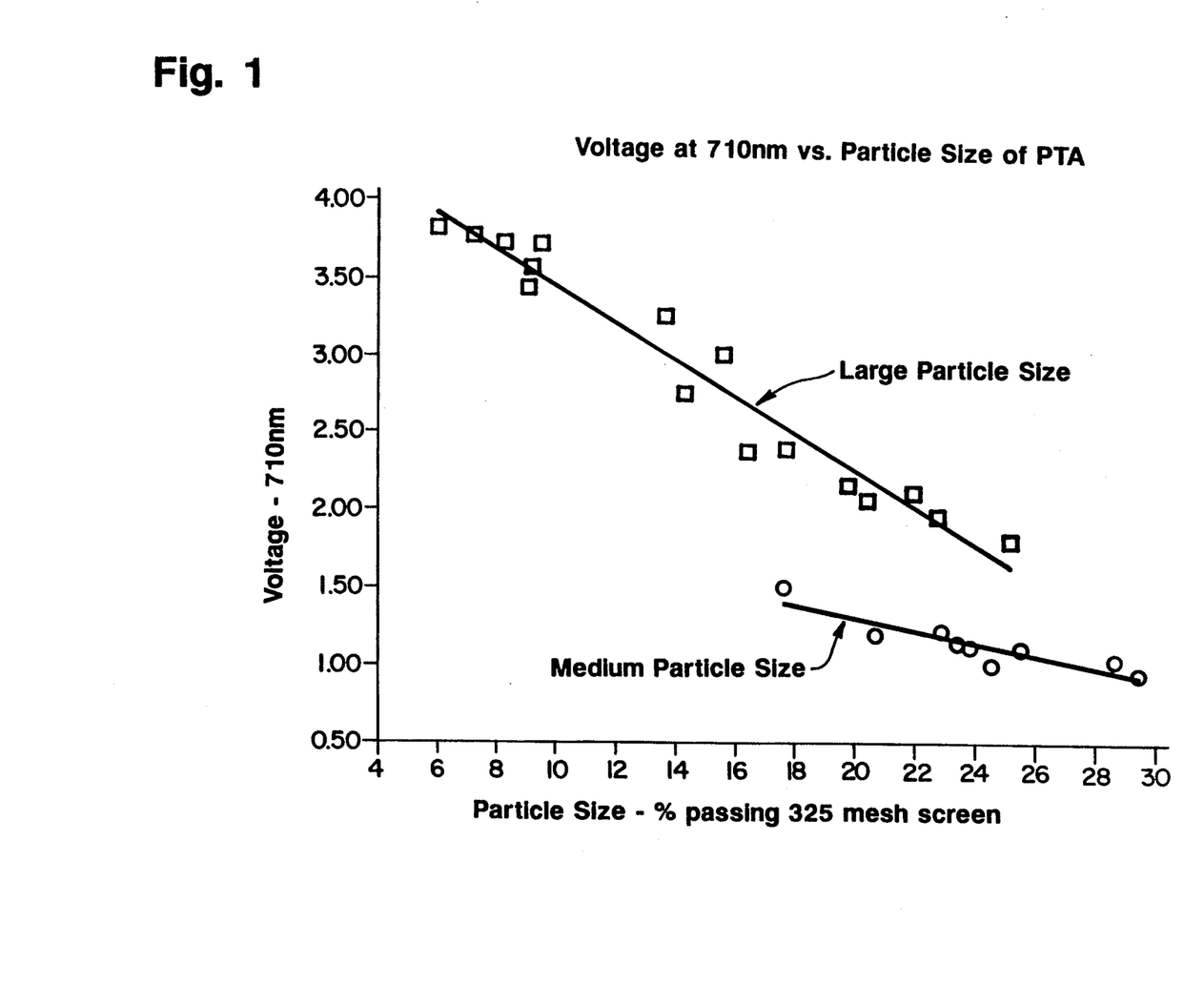

The voltage at 710 nm was found to correlate with particle size as measured by passage through a 325 mesh screen. Details are in Table I as to a large particle PTA size. Details are in Table II as to a smaller particle PTA size. FIG. 1 illustrates that the intensity of reflected light as measured by the voltage generated at 710 nm inversely relates to percent of particle sizes passing through a 325 mesh screen, U.S. Standard.

TABLE I

Effect of PTA Particle Size on Reflected Light Intensity Detector Response at 710 nm vs. 325 Mesh Screen Data Large Particle Size PTA

| Sample | Particle Size 325 Mesh Screen (% passing) | Wavelength 710 nm (volts) |
| --- | --- | --- |
| 1 | 5.90 | 3.833 |
| 2 | 7.15 | 3.782 |
| 3 | 8.15 | 3.737 |
| 4 | 9.00 | 3.451 |
| 5 | 9.10 | 3.570 |
| 6 | 9.40 | 3.727 |
| 7 | 13.55 | 3.262 |
| 8 | 14.20 | 2.760 |
| 9 | 15.50 | 3.011 |
| 10 | 16.35 | 2.379 |
| 11 | 17.65 | 2.413 |
| 12 | 19.70 | 2.154 |
| 13 | 20.30 | 2.070 |
| 14 | 21.85 | 2.115 |
| 15 | 22.65 | 1.959 |
| 16 | 25.10 | 1.812 |

TABLE II

Effect of PTA Particle Size on Reflected Light Intensity Detector Response at 710 nm vs. 325 Mesh Screen Data Small Particle Size PTA

| Sample | Particle Size 325 Mesh Screen (% passing) | Wavelength 710 nm (volts) |
| --- | --- | --- |
| 17 | 17.60 | 1.515 |
| 18 | 20.65 | 1.222 |
| 19 | 22.85 | 1.239 |
| 20 | 23.40 | 1.159 |
| 21 | 23.80 | 1.134 |
| 22 | 24.50 | 1.022 |
| 23 | 25.50 | 1.129 |
| 24 | 28.60 | 1.051 |
| 25 | 29.40 | 0.967 |

EXAMPLE II

Figure 2:
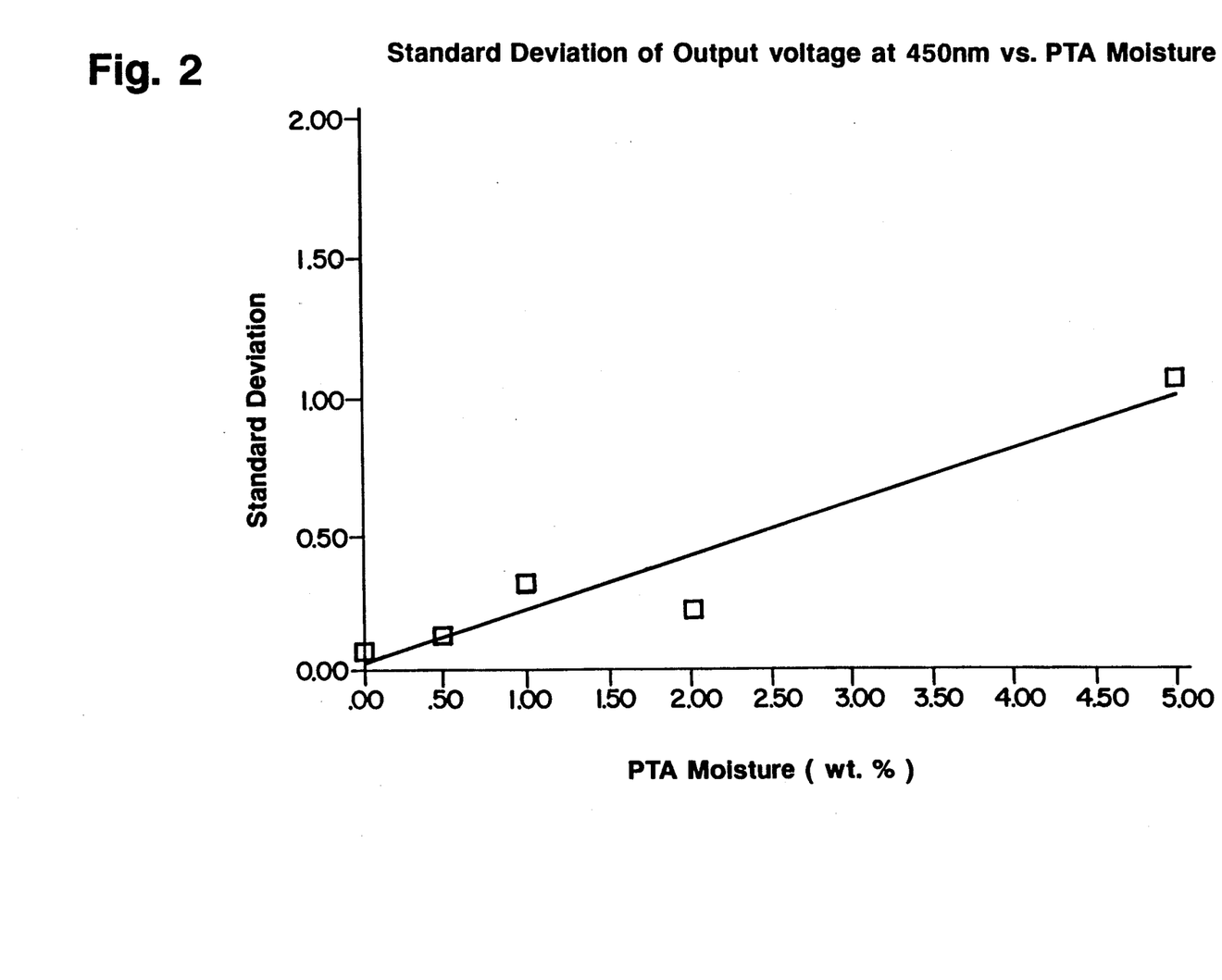
Figure 3:
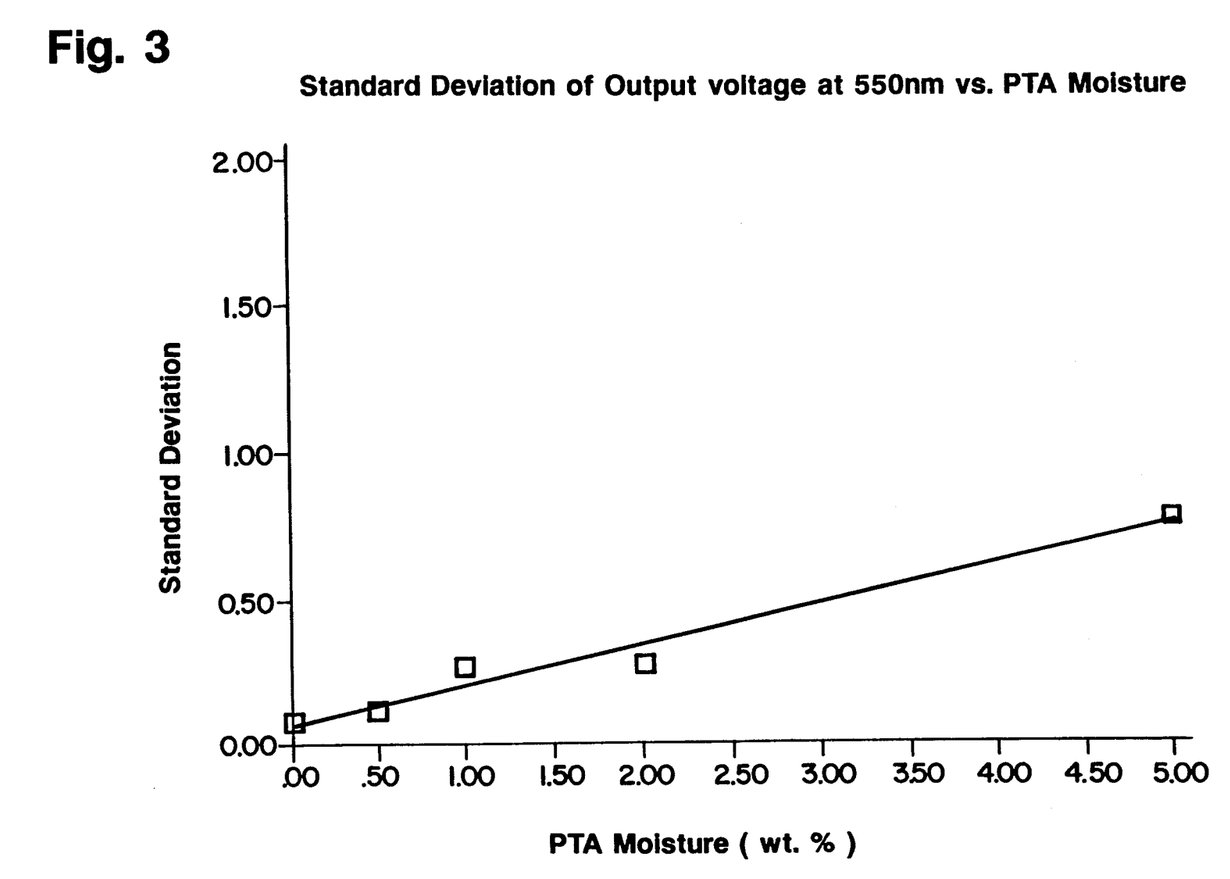
Figure 4:
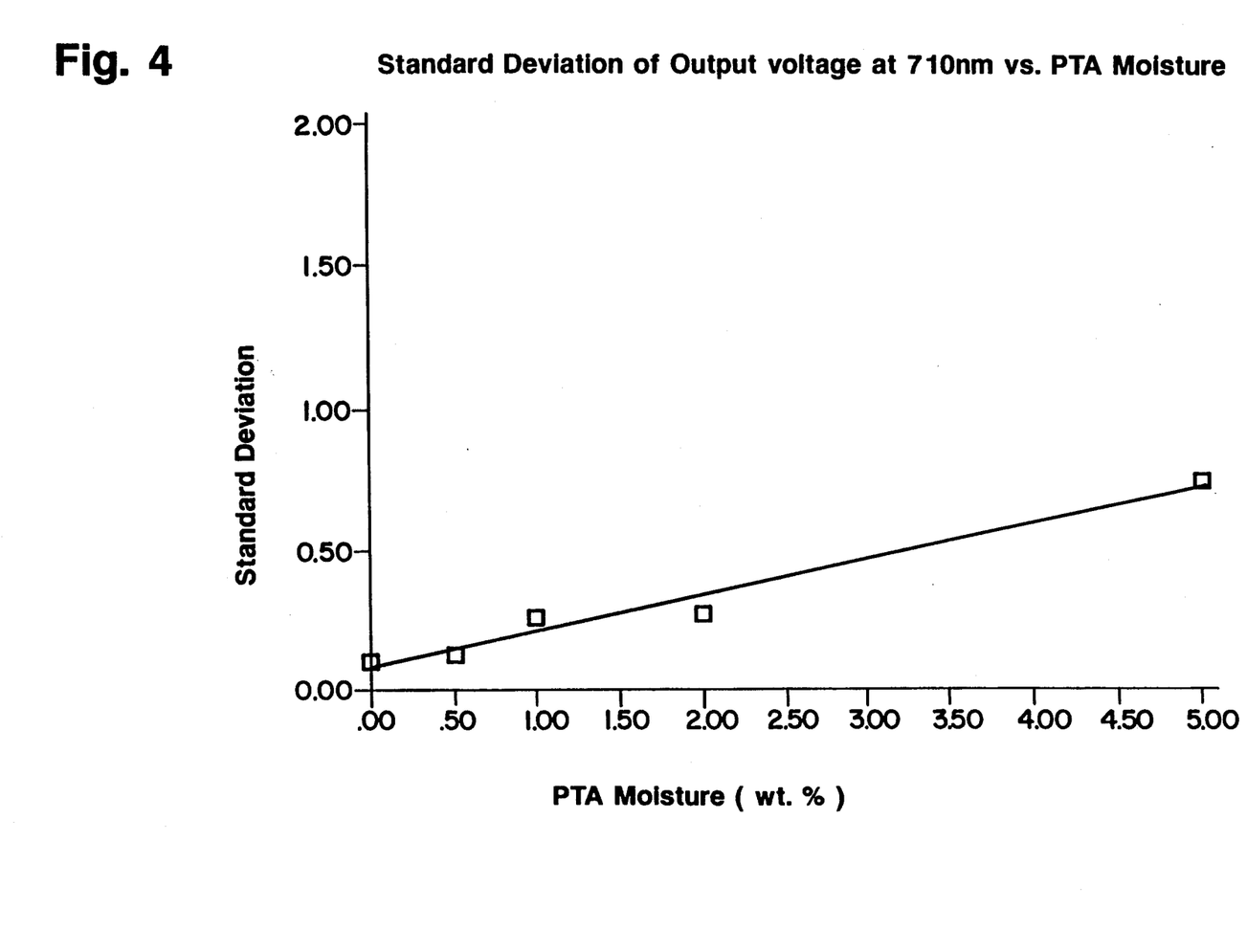

The procedure of Example I was repeated. Measurements were made at wavelengths of 450 nm, 550 nm, and 710 nm. Moisture content of samples related directly with on-line standard deviation wavelength voltage (SDWV) calculated basis the output voltages at the specified wavelengths. Details are in Table III. FIGS. 2, 3 and 4 illustrate that measurements of the SDWV correlate with PTA moisture content from 0 wt. % to about 5 wt. % moisture at wavelengths of 450 nm, 550 nm and 710 nm.

TABLE III

Effect of Moisture on On-Line SDWV Measurements

| Moisture (%) | On Line Output Voltages at Wavelengths (nm) of: | | |
| --- | --- | --- | --- |
| | 450 | 550 | 710 |
| 0.0% Moisture | | | |
| Mean | 1.35 | 1.81 | 1.90 |
| Std. Dev. | 0.07 | 0.08 | 0.10 |
| 0.5% Moisture | | | |
| Mean | 1.47 | 1.81 | 1.85 |
| Std. Dev. | 0.13 | 0.12 | 0.13 |
| 1.0% Moisture | | | |
| Mean | 1.86 | 2.11 | 2.16 |
| Std. Dev. | 0.32 | 0.26 | 0.25 |
| 2.0% Moisture | | | |
| Mean | 1.98 | 2.24 | 2.29 |
| Std. Dev. | 0.22 | 0.27 | 0.27 |
| 5.0% Moisture | | | |
| Mean | 3.32 | 3.20 | 3.22 |
| Std. Dev. | 1.05 | 0.76 | 0.73 |

What is claimed is:

1. A process for on-line monitoring of particle size and moisture content of finely-divided material in a product stream wherein said material reflects scattered light sufficient for detection by a photodetector, the light is of a wavelength within the range of from about 350 nanometers to about 1200 nanometers, particle size of said material is from about 1 micron to about 300 microns and moisture content is no greater than 10 weight percent of said material, which process comprises:
   a. a sampling means comprising a sampling vessel located in said product stream wherein said sampling vessel contains a discharge means to discharge continuously or periodically;
   b. a reference light source;
   c. a spectrophotometric analyzer having a plurality of photodetectors for the characterization of wavelengths of scattered light within the range of from about 350 nanometers to about 1200 nanometers;
   d. a communication means, having a first end connected to the light source and a second end extending into the sampling means;
   e. a light transmission means capable of transmitting scattered light of wavelengths from about 350 nanometers to about 1200 nanometers from the sampling means to the plurality of photodetectors within the spectrophotometric analyzer;
   f. a signal processor means in communication with the plurality of photodetectors for processing the characteristics of the said wavelengths to quantify the photodetector responses in volts to (i) measure the percent particles of said finely-divided material of particle size within the range of from about 1 micron to about 300 microns as measured by the voltage generated by a photodetector which measures the intensity of scattered light of a selected wavelength wherein said selected wavelength is within the range of from about 350 nanometers to about 1200 nanometers; and (ii) to measure the moisture content of said finely-divided material by the standard deviation of measurements of voltages generated by a photodetector which measures the said intensity of said scattered light of at least one wavelength within the range of from about 350 nanometers to about 1200 nanometers.

2. The process of claim 1 wherein said finely-divided material is selected from the group consisting of terephthalic acid, trimellitic acid, phthalic acid, 2,6-naphthalene dicarboxylic acid, trimellitic anhydride, phthalic anhydride, benzoic acid, polypropylene, polyethylene and clays wherein said finely-divided material comprises particles of 300 microns or less in size.

3. The process of claim 1 wherein moisture is selected from the group consisting of water, liquid, organic acids of from 2 to 8 carbon atoms, alcohols of from 1 to 12 carbon atoms, polyols of from 2 to 16 carbon atoms, hyboxy-terminated esters and ethers having molecular weights of up to about 500, and mixtures thereof.

4. The process of claim 3 wherein said moisture is selected from the group consisting of water, acetic acid and mixtures thereof.

5. The process of claim 1 wherein said finely-divided material is terephthalic acid and percent of particles of size of from about 10 microns to about 50 microns is measured by voltage generated by said photodetector in measuring intensity of scattered light of said selected wavelength within the range of from about 400 nanometers to about 750 nanometers.

6. The process of claim 5 wherein said selected wavelength is within the range of from about 550 nanometers to about 750 nanometers.

7. The process of claim 5 wherein said selected wavelength is about 710 nanometers.

8. The process of claim 5 wherein percent particles of particle size of from about 10 microns to about 50 microns is measured and is in the range of from about 2 wt. % to about 50 wt. % of total weight of said finely-divided material.

9. The process of claim 1 wherein said finely-divided material is terephthalic acid, and moisture content of said terephthalic acid is within the range of from about 0.01 wt. % to about 7.0 wt. % of total weight of said finely-divided material.

10. The process of claim 9 wherein the standard deviation of measurements of voltages generated by a photodetector, which measures intensity of scattered light of at least one wavelength within the range of from about 400 nanometers to about 750 nanometers, measures the moisture content of said terephthalic acid.

11. The process of claim 10 wherein said terephthalic acid is a product of a prior drying process and said standard deviation of said measurements generated by said photodetector comprises a feedback signal to control throughput rate and drying temperature of said drying process.

12. The process of claim 11 wherein said feedback signal is applied to said drying process continuously to control said throughput rate and said drying temperature.

13. The process of claim 9 wherein said moisture content comprises water.

14. The process of claim 1 wherein said sampling means comprises a receptacle mounted in the process stream to provide continuous or intermittent means of sampling said process stream.

* * * * *

UNITED STATES PATENT AND TRADEMARK OFFICE
CERTIFICATE OF CORRECTION

PATENT NO. : 5,062,709

DATED : November 5, 1991

INVENTOR(S) : Slee

It is certified that error appears in the above-identified patent and that said Letters Patent is hereby corrected as shown below:

Column 1, Line 9 "photodector" should read --photodetector--.

Abstract 7 "invention is futther" should read --invention is further--.

Signed and Sealed this

Twentieth Day of April, 1993

Attest:

MICHAEL K. KIRK

*Attesting Officer*   Acting Commissioner of Patents and Trademarks